US011039846B2

(12) United States Patent
Algawi et al.

(10) Patent No.: US 11,039,846 B2
(45) Date of Patent: Jun. 22, 2021

(54) GUIDEWIRE MANIPULATOR

(71) Applicant: Biosense Webster (israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 289 days.

(21) Appl. No.: 15/926,738

(22) Filed: Mar. 20, 2018

(65) Prior Publication Data

US 2018/0303505 A1    Oct. 25, 2018

Related U.S. Application Data

(60) Provisional application No. 62/489,957, filed on Apr. 25, 2017.

(51) Int. Cl.
| *A61B 17/24* | (2006.01) |
| *A61M 25/09* | (2006.01) |
| *A61M 29/02* | (2006.01) |
| *A61M 25/01* | (2006.01) |

(Continued)

(52) U.S. Cl.
CPC ......... *A61B 17/24* (2013.01); *A61M 25/0113* (2013.01); *A61M 25/09* (2013.01); *A61M 25/09041* (2013.01); *A61M 29/02* (2013.01); *A61B 2017/00526* (2013.01); *A61M 25/1006* (2013.01); *A61M 2025/09008* (2013.01);

(Continued)

(58) Field of Classification Search
CPC .. A61M 25/01; A61M 25/0113; A61M 25/09; A61M 25/09041; A61M 29/02; A61M 25/1006; A61M 2025/09008; A61M 2025/09018; A61M 2025/09116; A61M 2025/09133; A61B 17/24
USPC .................................................. 606/585, 108
See application file for complete search history.

(56) References Cited

U.S. PATENT DOCUMENTS

| 6,673,101 | B1 * | 1/2004 | Fitzgerald | A61F 2/95 604/161 |
| 10,561,440 | B2 * | 2/2020 | Look | A61B 17/22 |

(Continued)

FOREIGN PATENT DOCUMENTS

| WO | WO 94/16762 | 8/1994 |
| WO | WO 2013/155409 | 10/2013 |

OTHER PUBLICATIONS

European Search Report dated Dec. 18, 2018 from corresponding European Patent Application No. 18168995.1.

*Primary Examiner* — Kathleen S Holwerda
*Assistant Examiner* — Kankindi Rwego
(74) *Attorney, Agent, or Firm* — Frost Brown Todd LLC

(57) ABSTRACT

A manipulator, including an elongated chassis containing a U-shaped channel defining a distal direction and a proximal direction. The manipulator also includes an adjuster that is configured to slide in the U-shaped channel. The adjuster includes a first wheel which on rotation translates a guidewire positioned in the adjuster along an axis of the guidewire, and a second wheel which on rotation rotates the guidewire positioned in the adjuster about the axis of the guidewire. The adjuster also includes a port, distal to the first and the second wheel, that is configured to accept a tubular balloon and the guidewire.

30 Claims, 14 Drawing Sheets

(51) Int. Cl.
*A61B 17/00* (2006.01)
*A61M 25/10* (2013.01)

(52) U.S. Cl.
CPC ............ *A61M 2025/09108* (2013.01); *A61M 2025/09116* (2013.01); *A61M 2025/09133* (2013.01)

(56) References Cited

U.S. PATENT DOCUMENTS

| | | | |
|---|---|---|---|
| 2005/0197557 A1* | 9/2005 | Strommer | A61M 25/0113 600/407 |
| 2005/0245847 A1* | 11/2005 | Schaeffer | A61M 25/09041 600/585 |
| 2006/0041245 A1 | 2/2006 | Ferry et al. | |
| 2009/0082722 A1* | 3/2009 | Munger | A61M 25/0113 604/95.01 |
| 2009/0105645 A1 | 4/2009 | Kidd et al. | |
| 2016/0082233 A1 | 3/2016 | Ha et al. | |
| 2017/0065396 A1* | 3/2017 | Look | A61B 17/320758 |
| 2017/0325841 A1 | 11/2017 | Govari | |

\* cited by examiner

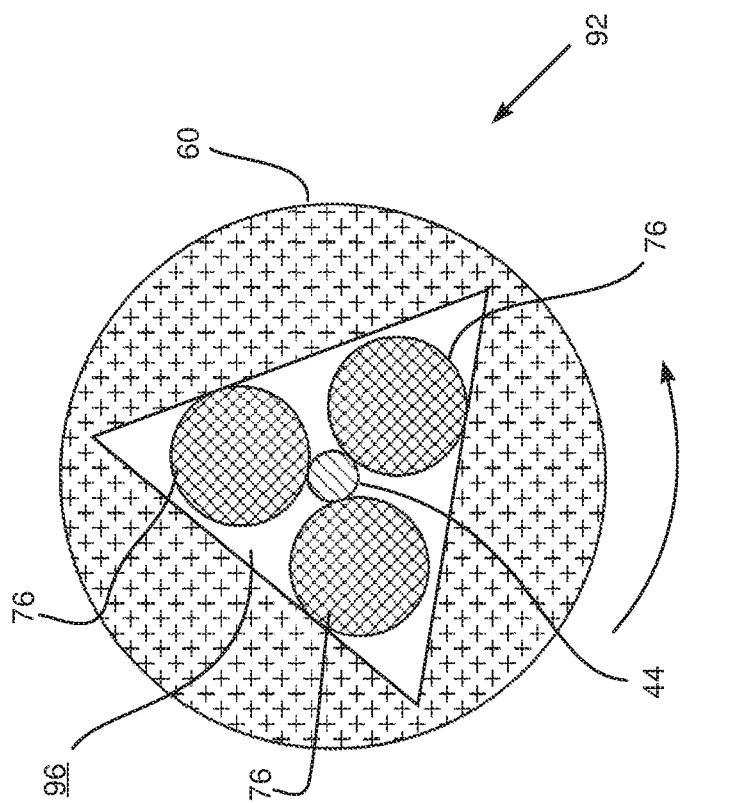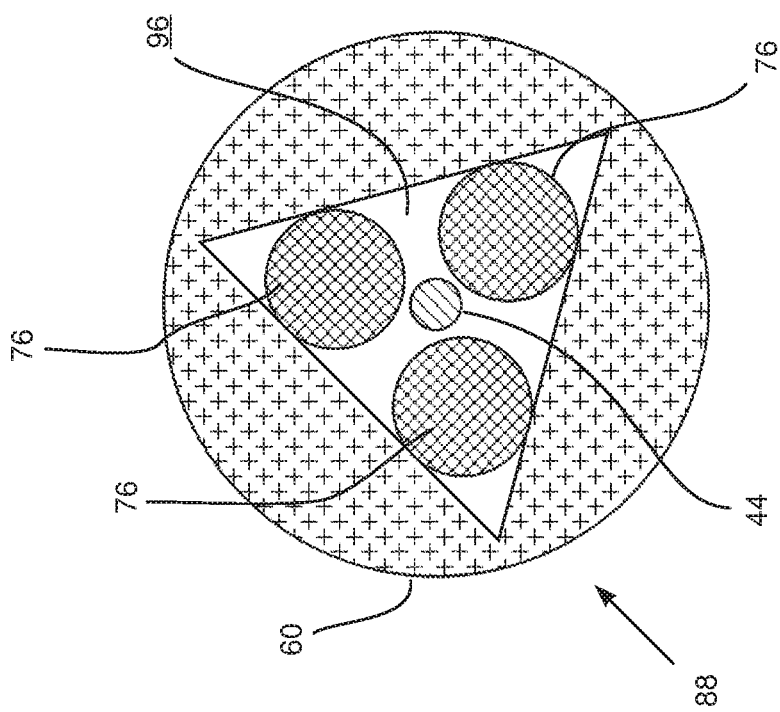
FIG. 7

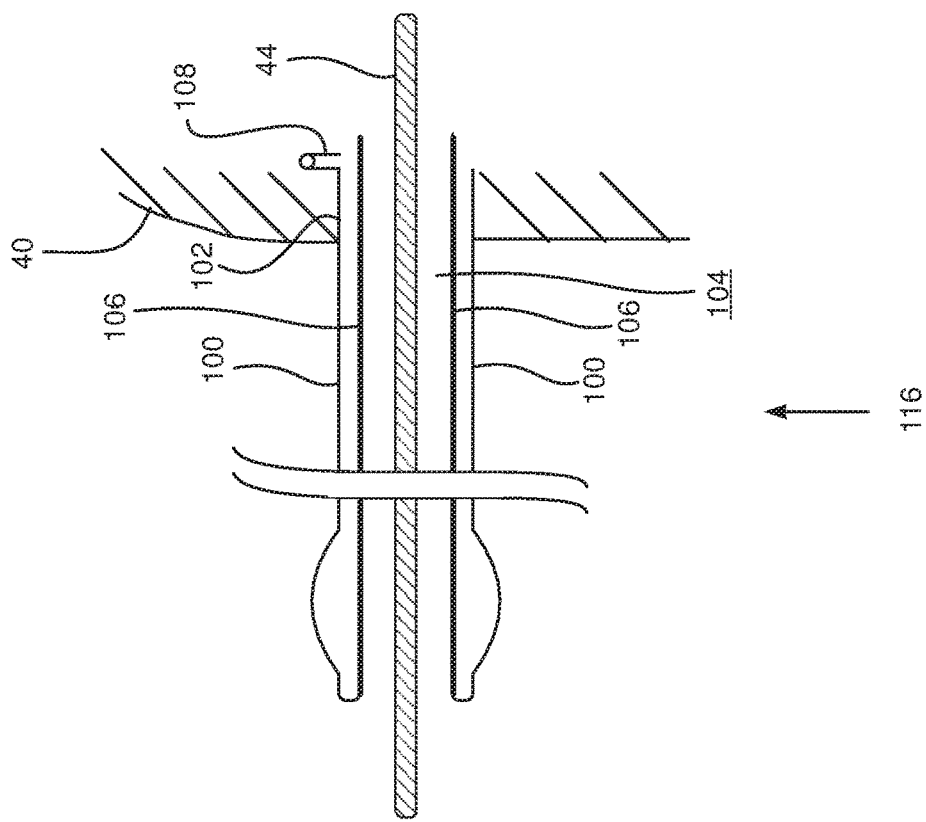
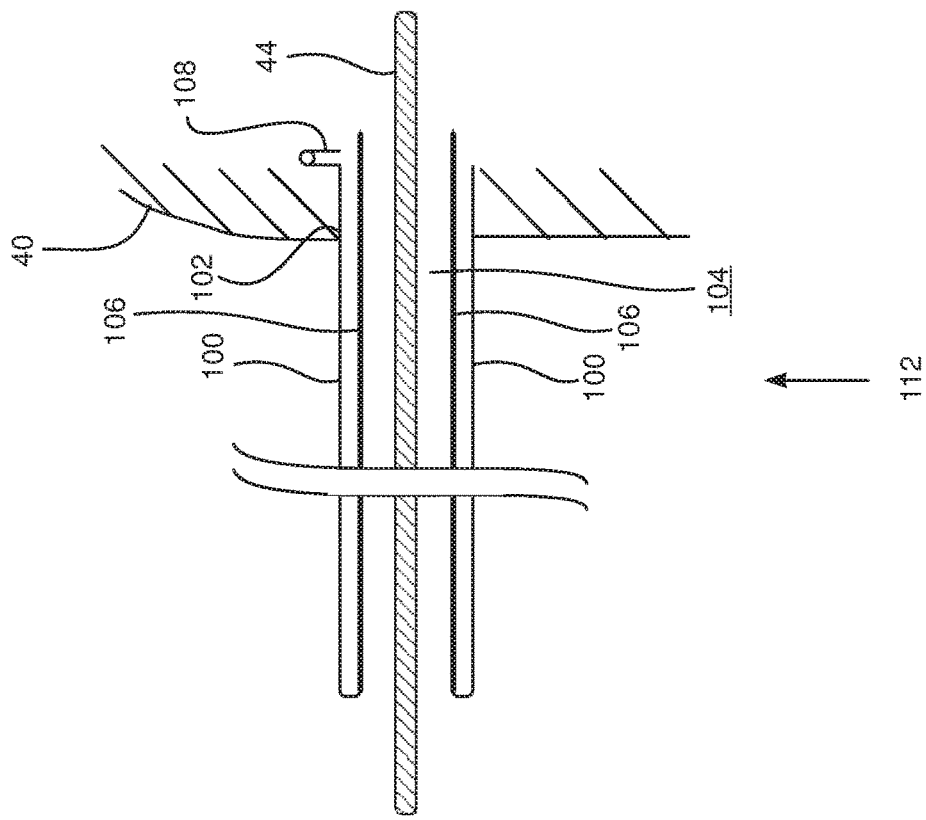
FIG. 8

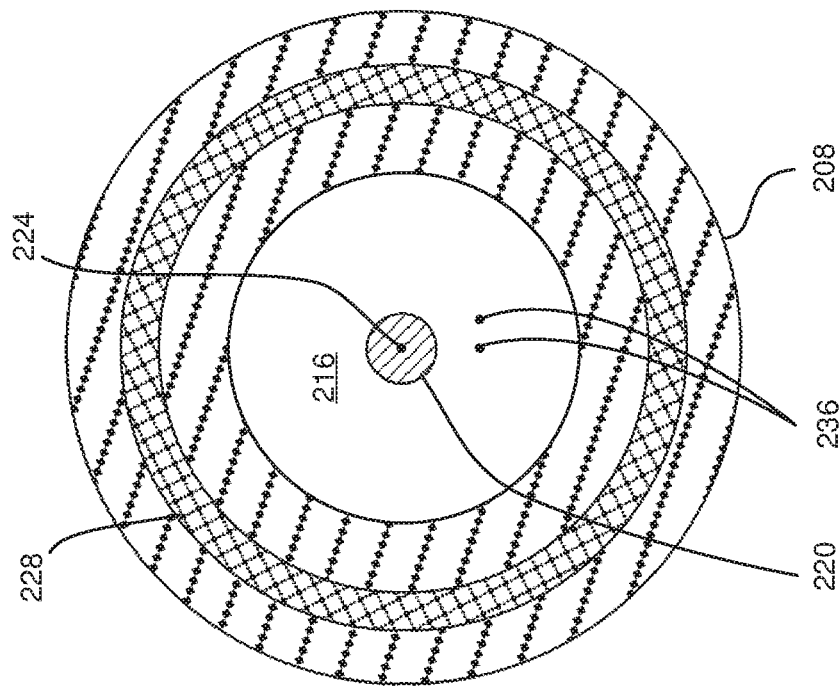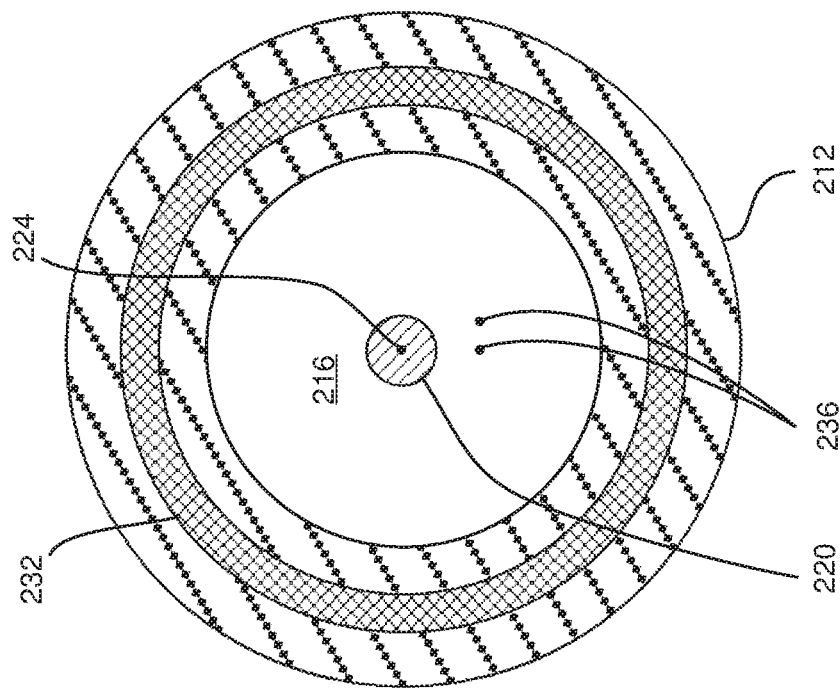
FIG. 13

GUIDEWIRE MANIPULATOR

CROSS-REFERENCE TO RELATED APPLICATION

This application claims the benefit of U.S. Provisional Patent Application 62/489,957, filed 25 Apr. 2017, which is incorporated herein by reference.

FIELD OF THE INVENTION

This invention relates generally to sinuplasty, and specifically to manipulation of instruments used in the sinuplasty.

BACKGROUND OF THE INVENTION

Balloon sinuplasty is a procedure that ear, nose and throat surgeons may use for the treatment of blocked sinuses. The procedure involves inserting a balloon over a wire guidewire to a sinus passageway. After insertion, the balloon is inflated with the goal of widening the walls of the sinus passageway.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a manipulator, including:

an elongated chassis containing a U-shaped channel defining a distal direction and a proximal direction; and an adjuster configured to slide in the U-shaped channel, the adjuster including:

a first wheel which on rotation translates a guidewire positioned in the adjuster along an axis of the guidewire;

a second wheel which on rotation rotates the guidewire positioned in the adjuster about the axis of the guidewire; and a port, distal to the first and the second wheel, configured to accept a tubular balloon and the guidewire.

Typically, the first wheel includes a first wheel axle, the adjuster further including retaining slots configured to accept the axle, so that on rotation of the first wheel about the first wheel axle the first wheel slides in the retaining slots to engage the guidewire.

In a disclosed embodiment the second wheel rotates about a second wheel axis, the adjuster further including a plurality of cylinders enclosed by the second wheel and having respective axes parallel to the second wheel axis, so that on rotation of the second wheel about the second wheel axis, the cylinders move orthogonally to their axes to engage the guidewire. The second wheel may contain an open triangular portion, and the plurality of cylinders consists of three cylinders located at respective apices of the triangular portion. Typically, on rotation of the second wheel about the second wheel axis, the cylinders are pushed inwards by sides of the triangular portion so as to engage the guidewire.

In a further disclosed embodiment the balloon is attached in a fluid-tight manner to the port at a proximal end of the balloon.

In a yet further disclosed embodiment the manipulator includes a balloon retaining tube, traversing the port, attached to a distal end of the balloon.

In an alternative embodiment the U-shaped channel contains a passage configured to restrain the balloon and the guidewire from deviating out of the passage. Typically, the balloon translates along the passage when the adjuster slides in the U-shaped channel.

In a further alternative embodiment the manipulator includes a rigid tube, removably attached to the elongated chassis, configured to accept the tubular balloon and the guidewire. Typically, the rigid tube is attached in a position not in line with the elongated chassis.

There is further provided, according to an embodiment of the present invention, a guidewire, including:

a plastic tube forming a lumen, the plastic tube being configured to be inserted into a nasal sinus and having a length;

a braid incorporated into the plastic tube; and a metal wire located in the lumen along the length of the plastic tube.

In a disclosed embodiment the plastic tube includes a first plastic tube cemented to a second plastic tube, and the lumen is common to the first and second tubes. The first and the second plastic tubes may have differing flexibilities. The first and the second plastic tubes may have differing thicknesses.

There is further provided, according to an embodiment of the present invention, a method, including:

providing an elongated chassis containing a U-shaped channel defining a distal direction and a proximal direction; and sliding an adjuster in the U-shaped channel, the adjuster including:

a first wheel which on rotation translates a guidewire positioned in the adjuster along an axis of the guidewire, a second wheel which on rotation rotates the guidewire positioned in the adjuster about the axis of the guidewire, and a port, distal to the first and the second wheel, configured to accept a tubular balloon and the guidewire.

There is also provided, according to an embodiment of the present invention, a method, including:

forming a lumen in a plastic tube, the plastic tube being configured to be inserted into a nasal sinus and having a length;

incorporating a braid into the plastic tube; and locating a metal wire in the lumen along the length of the plastic tube.

The present disclosure will be more fully understood from the following detailed description of the embodiments thereof, taken together with the drawings, in which:

BRIEF DESCRIPTION OF THE DRAWINGS

FIG. 7 shows schematic cross-sections of a wheel of the adjuster, according to an embodiment of the present invention;

FIG. 8 shows schematic cross-sections of a balloon attached to the adjuster, according to an embodiment of the present invention;

FIGS. 12, 13, and 14 schematically illustrate a guidewire, according to an embodiment of the present invention.

DETAILED DESCRIPTION OF EMBODIMENTS

Figure 1:
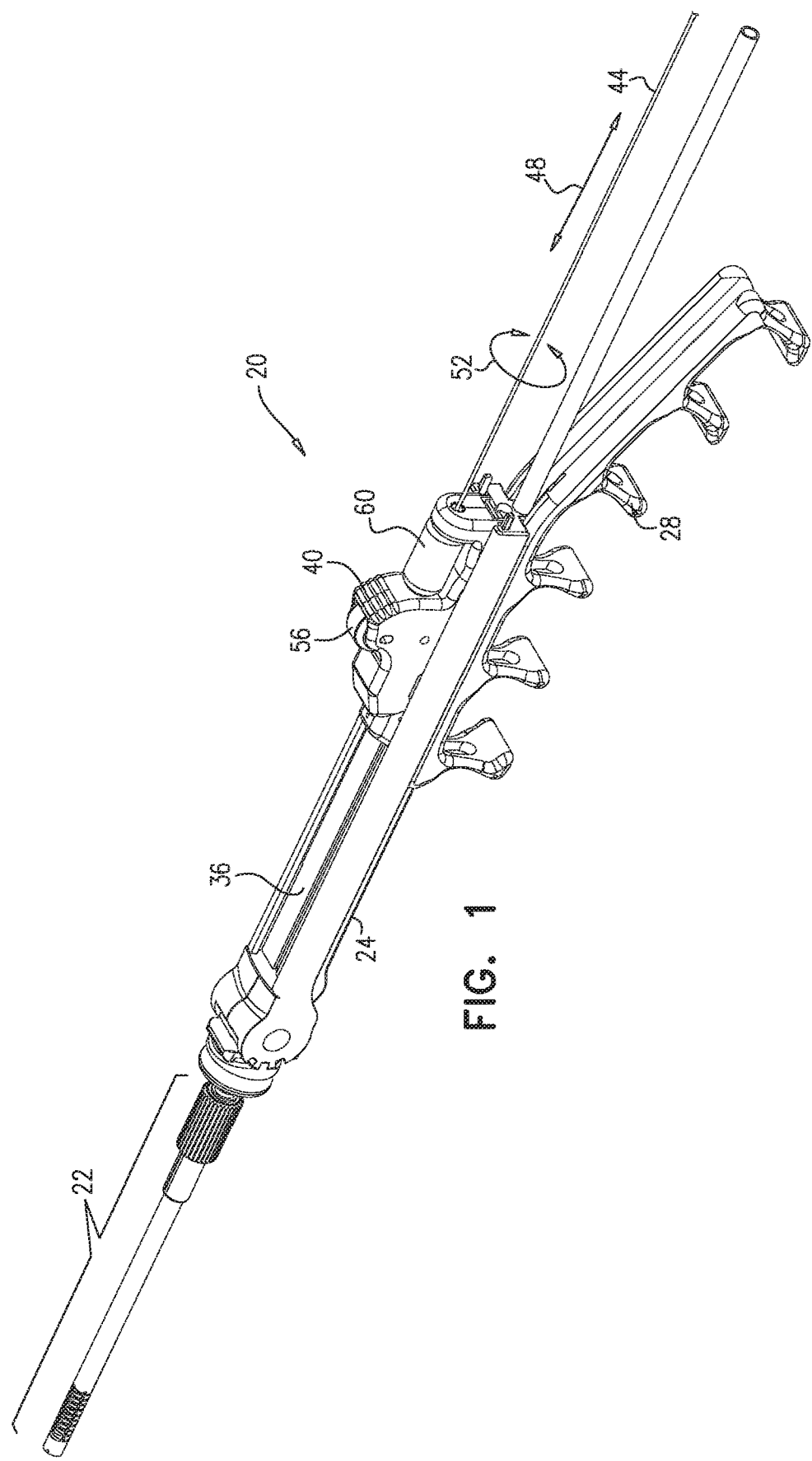
FIG. 1 is a schematic perspective view of a sinuplasty guidewire and balloon manipulator, according to an embodiment of the present invention.
Figure 2:
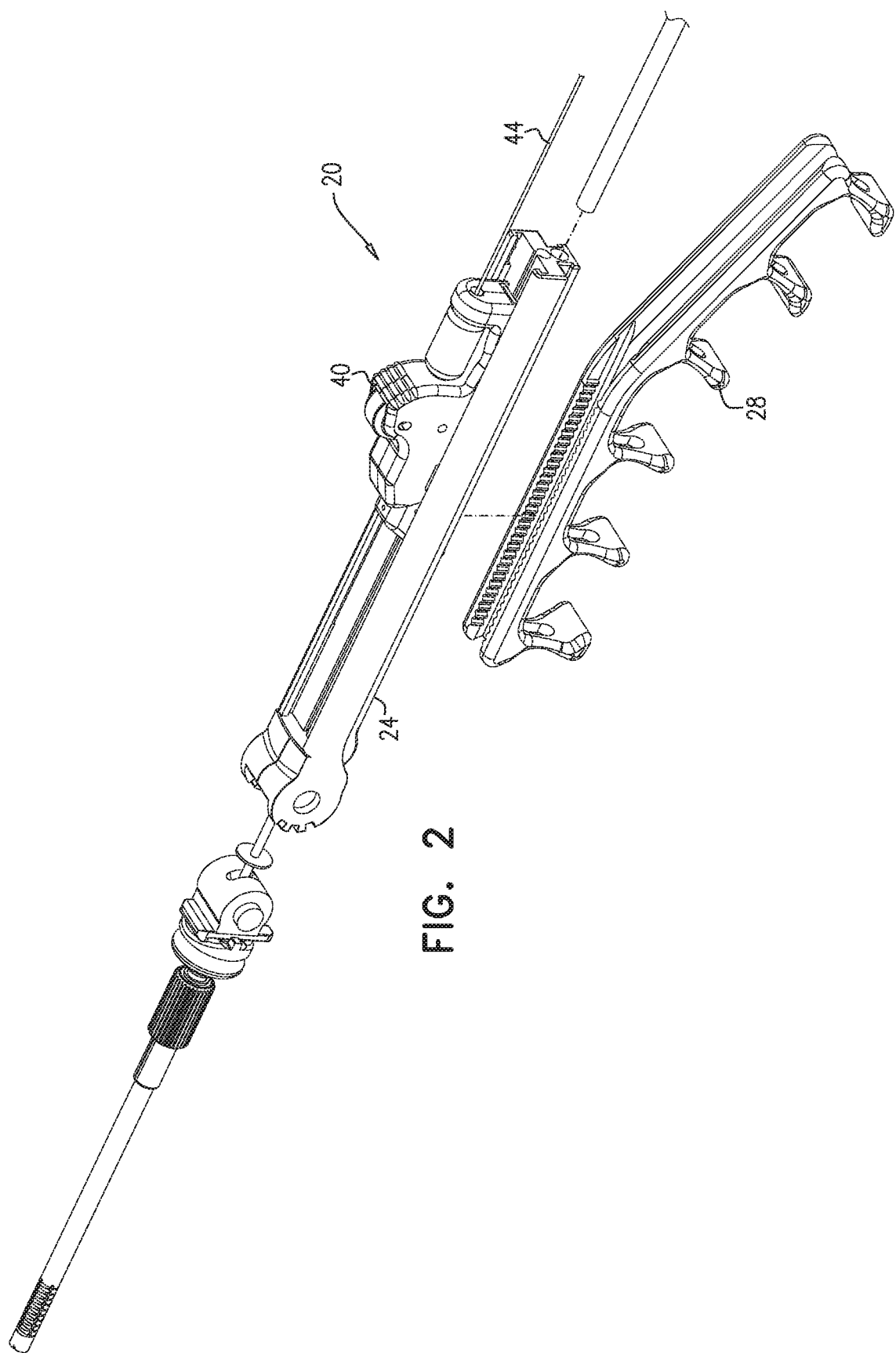
FIG. 2 is a partly exploded view of the manipulator, according to an embodiment of the present invention.
Figure 3:
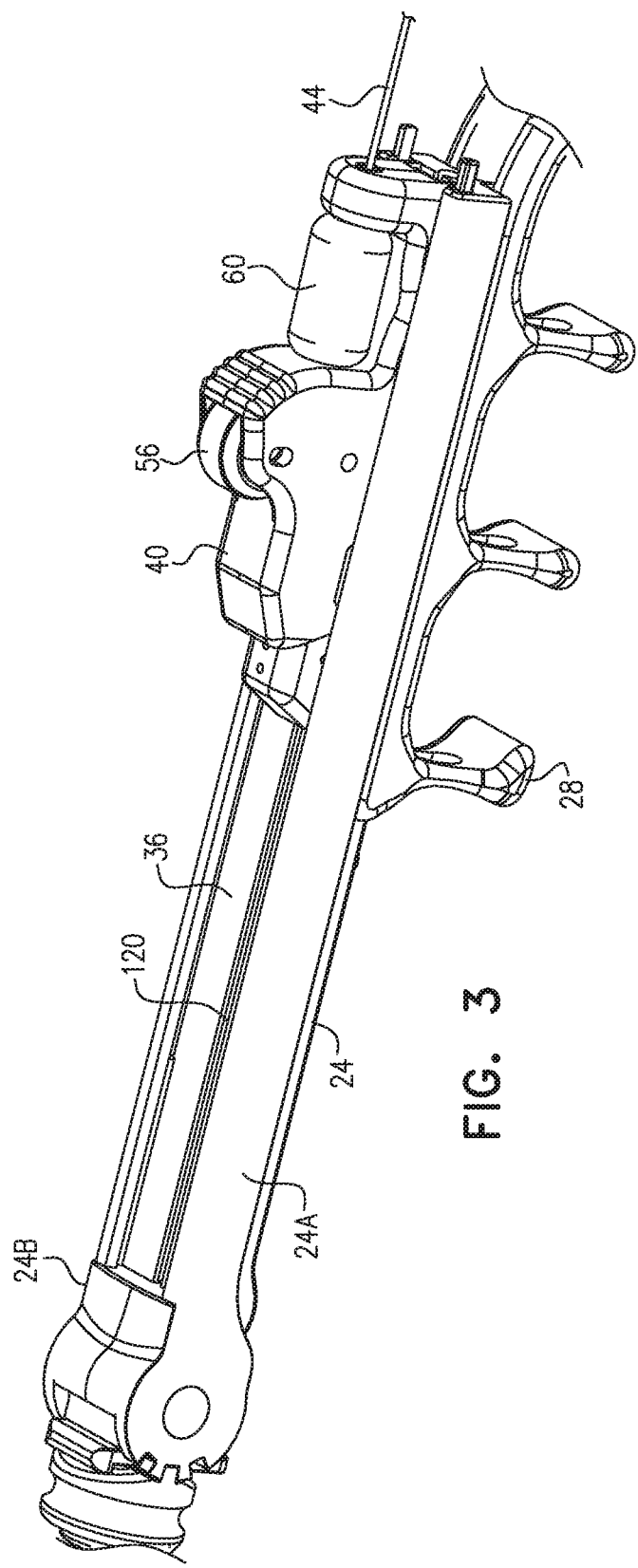
FIG. 3 is an enlarged section of the exploded view as seen from above, according to an embodiment of the present invention.
Figure 4:
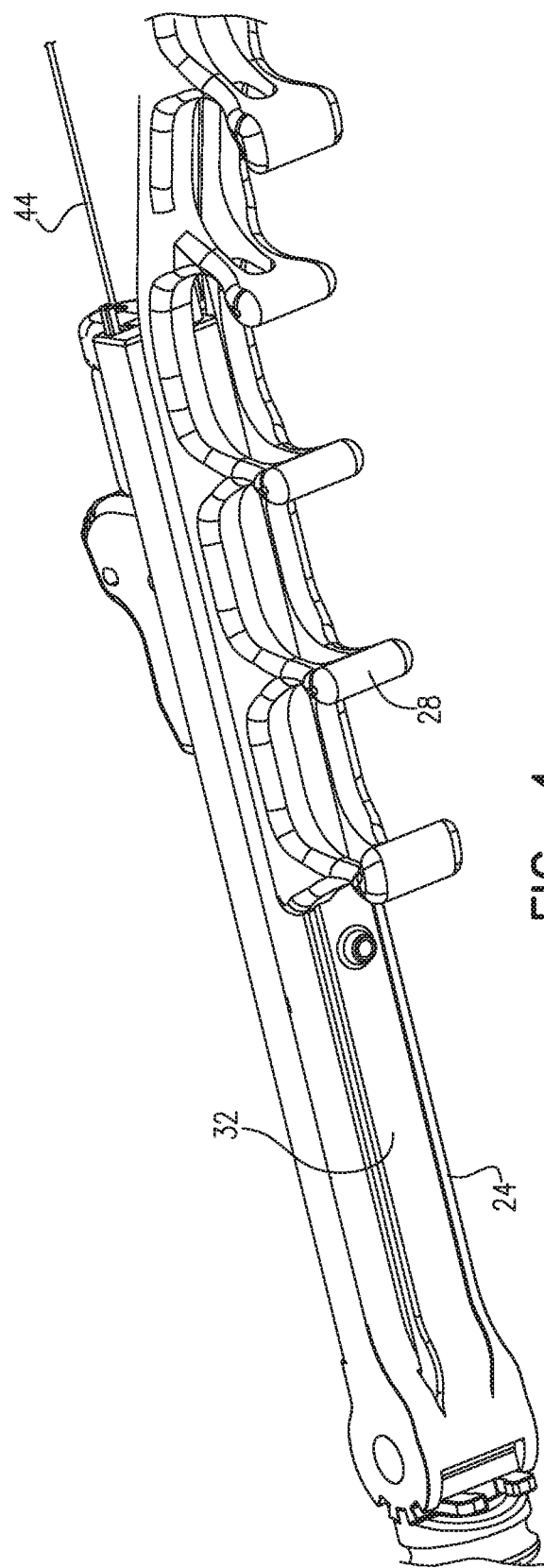
FIG. 4 is an enlarged section of the exploded view as seen from below, according to an embodiment of the present invention.

FIG. 1 is a schematic perspective view of a sinuplasty guidewire and balloon manipulator 20, FIG. 2 is a partly exploded view of the manipulator, FIG. 3 is an enlarged section of the exploded view as seen from above, and FIG. 4 is an enlarged section of the exploded view as seen from below, according to an embodiment of the present invention. As is described in more detail below, manipulator 20 is configured to enable a physician performing a sinuplasty procedure to single-handedly manipulate a guidewire used for the procedure, as well as to advance and retract a balloon used in the procedure. A distal section 22 of the manipulator is also described below.

Manipulator 20 comprises an elongated generally U-shaped chassis 24 to which is movably attached a chassis holder 28. In one embodiment chassis 24 is formed as two mirror image sections 24A, 24B which are cemented together. Holder 28 is designed to be held by and conform to the fingers of the physician, and the holder may be positioned and fixed distally/proximally with respect to the chassis by sliding the holder along a ridge 32 formed in the external base of chassis 24.

Retained within a U-shaped channel 36 of the chassis is a guidewire position adjuster 40. The channel defines distal and proximal directions for the chassis. As explained in more detail below, adjuster 40 enables the physician holding the manipulator to translate and rotate a guidewire 44 passing through the adjuster. The translation, which may be in a distal direction or a proximal direction, is along an axis of the guidewire, as illustrated by a double-headed arrow 48, and the rotation is around an axis of the guidewire, as illustrated by a double-headed arrow 52. The translation and rotation may be performed by a single finger, or the thumb, of the physician's hand holding the manipulator. (As is also described below, adjuster 40 enables the physician to translate and inflate a sinuplasty balloon attached to the adjuster. The adjuster typically comprises channels for the inflation, which may be performed by a device such as a pump connected to the adjuster.)

Adjuster 40 comprises three wheels, a first wheel 56 which is rotatable about an axis orthogonal to the axis of guidewire 44, a second wheel 60 which is rotatable about an axis parallel to the axis of the guidewire, and a third wheel 72 which has a rotation axis parallel to the axis of wheel 56. Wheel 72 is internal to adjuster 40, and so is not visible in FIGS. 1-4, but is illustrated in FIG. 6 below.

Figure 5:
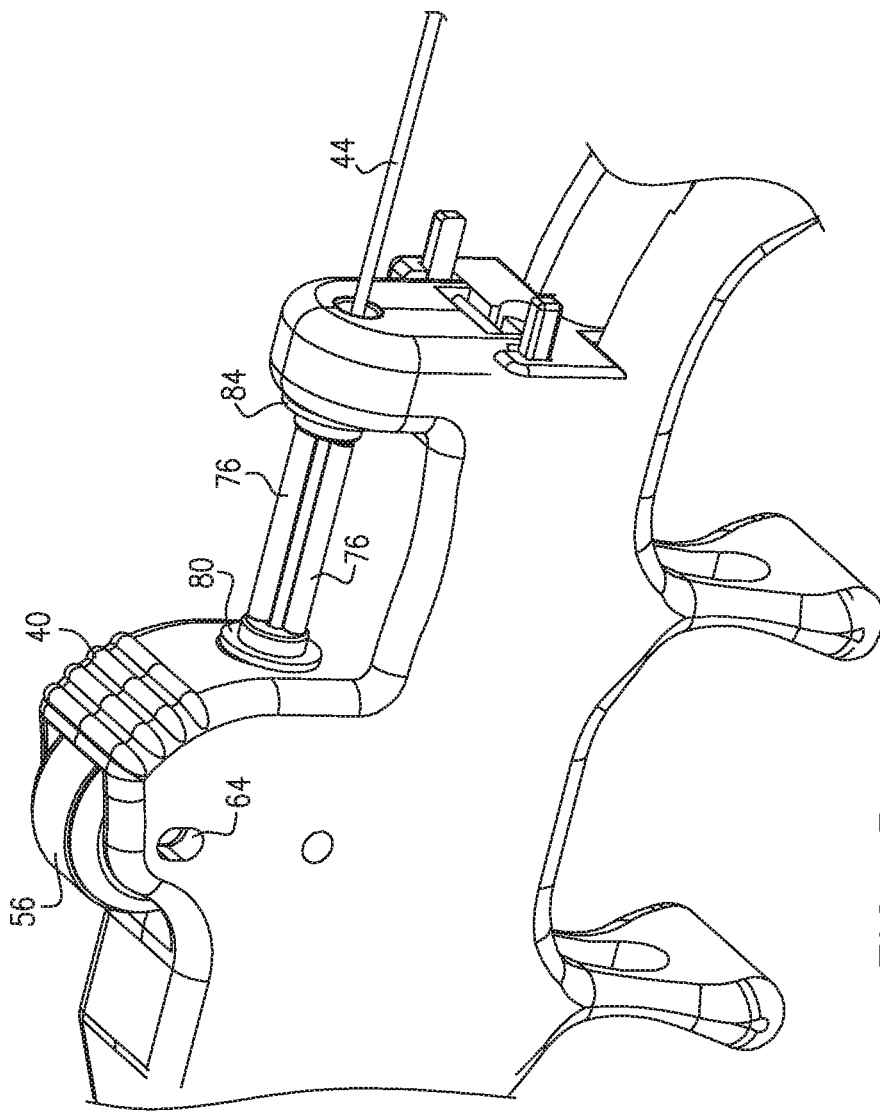
FIG. 5 and FIG. 6 illustrate an adjuster of the manipulator, according to an embodiment of the present invention.
Figure 6:
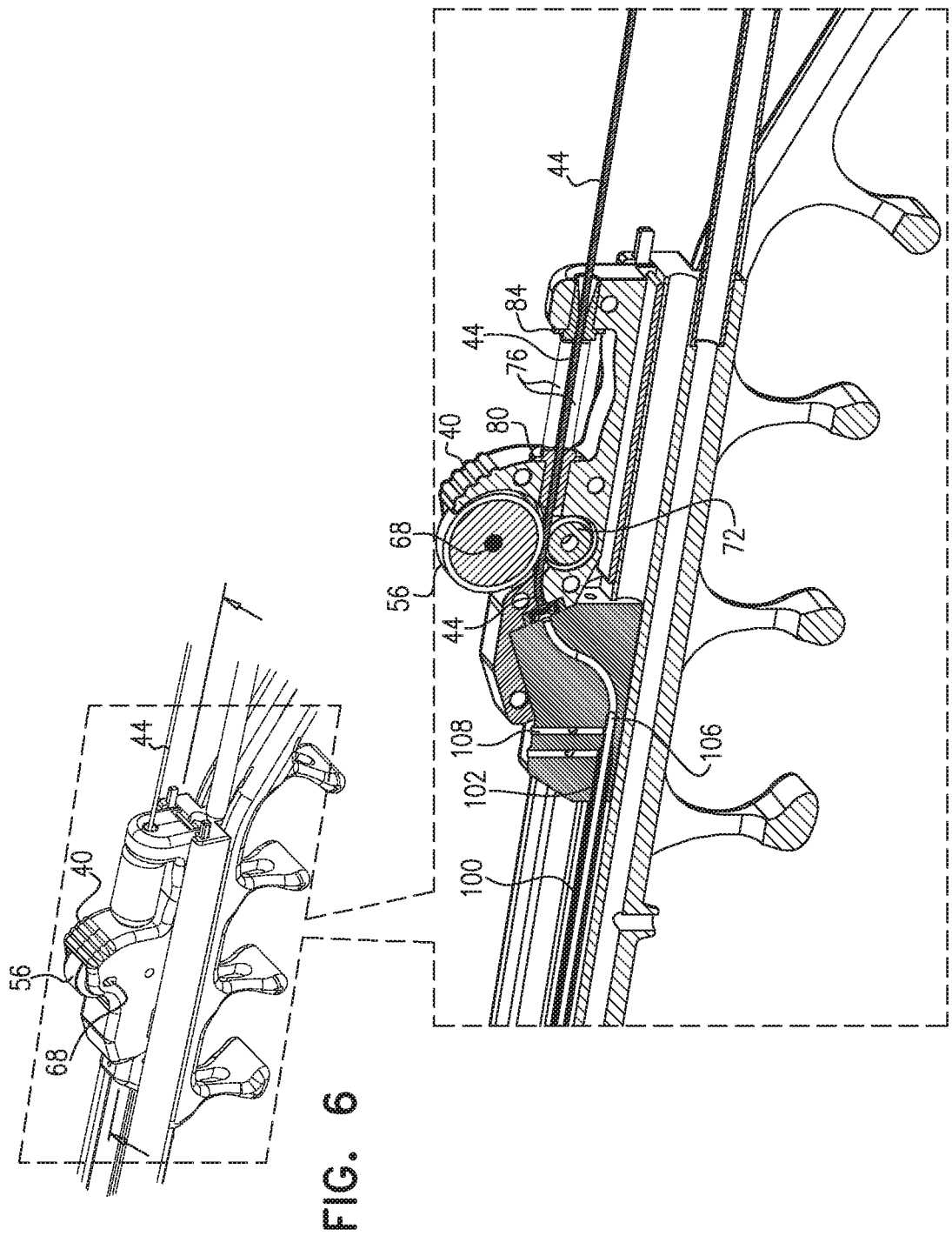

FIG. 5 and FIG. 6 illustrate adjuster 40, according to an embodiment of the present invention. In FIG. 5 second wheel 60 is not shown, so as to illustrate internal structure within the second wheel. FIG. 6 is a sectional illustration of adjuster 40 and a portion of manipulator 20, so as to illustrate internal structure related to first wheel 56.

As shown in FIG. 5, adjuster 40 comprises a slot 64 which retains an axle 68 (FIG. 6) of wheel 56. Slot 64 allows the axle, and its wheel, to move orthogonally with respect to the guidewire. In the absence of pressure from a finger of the physician, axle 68 is situated in the upper part of the slot and wheel 56, while contacting the guidewire, does not engage it. In this situation, the guidewire is free to move with respect to wheel 56.

When the physician applies pressure to wheel 56, for example by rotating the wheel with a finger or thumb, the axle 68 moves down in slot 64, so that wheel 56 engages guidewire 44 and presses the guidewire against a freely rotating wheel 72. Thus, while the physician applies pressure so as to rotate wheel 56, the guidewire translates along its axis, in the direction of arrow 48 (FIG. 1). Conversely, if the physician does not apply pressure to rotate wheel 56, the guidewire is not engaged by the wheel so is not constrained in a guidewire axial direction by the wheel.

Wheel 60 (FIG. 3) performs a generally similar function to wheel 56, so that in the case of the physician applying pressure on wheel 60 so as to rotate the wheel, the guidewire rotates about its axis, in the direction of arrow 52 (FIG. 1). On the other hand, if no pressure is applied, there is no engagement of the wheel with the guidewire, as explained below.

Within wheel 60, and enclosed by the wheel, are three generally similar cylinders 76, which have axes parallel to the axis of wheel 60. Cylinders 76 are arranged at the apices of an equilateral triangle, and the cylinders are retained in place by end portions 80 and 84 which also hold wheel 60.

FIG. 7 shows schematic cross-sections of wheel 60 in two states, according to an embodiment of the present invention. As shown in both diagrams 88 and 92, an internal portion 96 of wheel 60 has a generally triangular open cross-section. In a first "relaxed" state of wheel 60, schematically illustrated in diagram 88, wheel 60 is not rotated, and while cylinders 76 may contact guidewire 44 because of the force of gravity, there is substantially no frictional force preventing guidewire movement along its axis. In a second rotating state of the wheel, illustrated in diagram 92, cylinders 76 are pushed inwards by the sides of triangular portion 96, moving orthogonally to their axes, and so engage guidewire 44. The engagement causes the guidewire to rotate.

As is shown in FIG. 6, adjuster 40 is also attached in a watertight manner to a sinuplasty tubular balloon 100. As is described below, application of a fluid to the balloon causes the balloon to expand at its distal end.

FIG. 8 shows schematic cross-sections of balloon 100 as it is attached to a port 102 in adjuster 40, according to an embodiment of the present invention. Port 102 is at a distal end of adjuster 40, and thus is distal to wheels 56 and 60. Guidewire 44 exits from the adjuster, and passes through a central lumen 104 of tubular balloon 100. Balloon 100 is attached in an air/watertight, i.e., a fluid-tight, manner to port 102 at the balloon's proximal end. The balloon is also attached at its distal end to a balloon retaining tube 106, and the retaining tube traverses port 102 and is attached at its proximal end to adjuster 40. The balloon may be filled with a fluid, such as pressurized air or a saline solution, via a channel 108 (port 102, tube 106, and channel 108 are also shown in FIG. 6) incorporated in adjuster 40. A diagram 112 illustrates the balloon and the guidewire in the balloon's unexpanded state; a diagram 116 illustrates the balloon and the guidewire when the balloon has been expanded by injection of fluid (liquid or air) into the balloon via channel 108. For simplicity, other elements of manipulator 20, described below, are not shown in FIG. 8.

Figure 9:
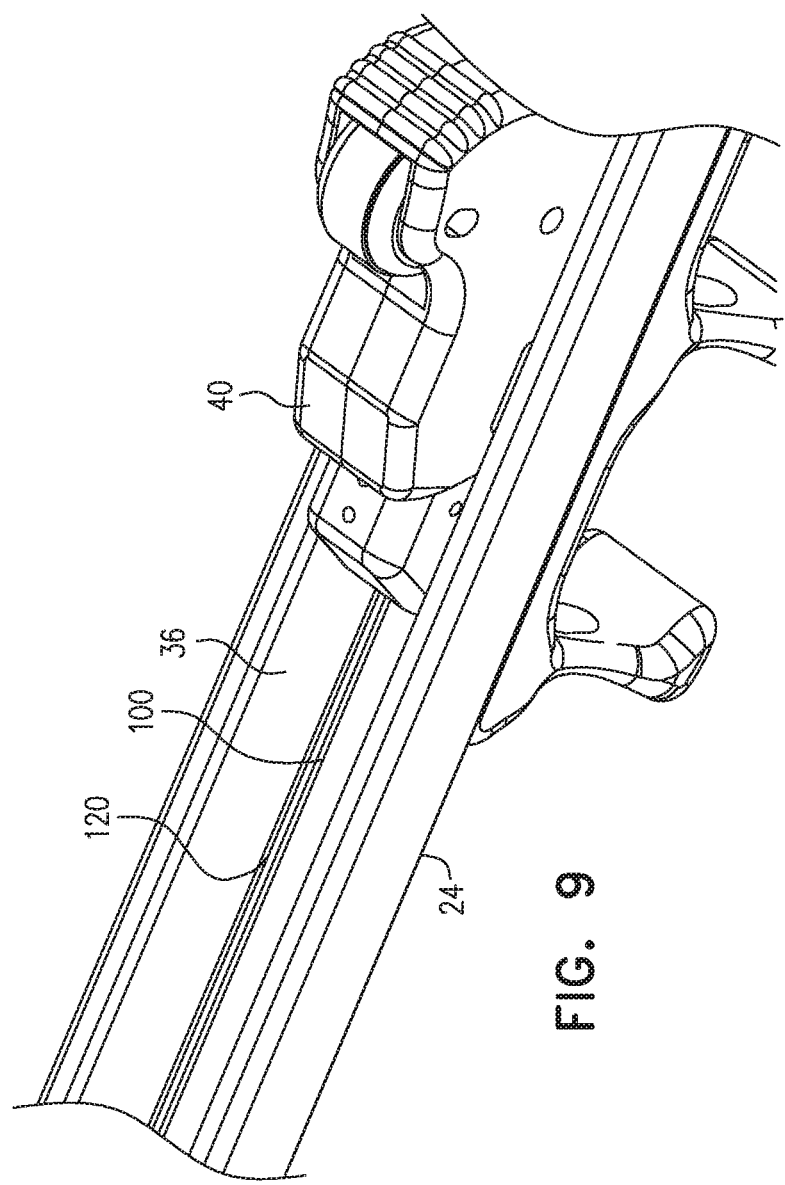
FIG. 9 illustrates a straight passage within a U-shaped channel of the manipulator, according to an embodiment of the present invention.

FIG. 9 illustrates a straight passage 120 within U-shaped channel 36, according to an embodiment of the present invention. (Passage 120 is also shown in FIG. 3.) Balloon 100 fits into passage 120, and the passage is configured to restrain the balloon, and also guidewire 44, from deviating out of the passage. Adjuster 40 is configured to be translatable in a distal direction or a proximal direction along U-shaped channel 36, and it will be understood that when it is translated, balloon 100 also translates in passage 120.

Figure 10:
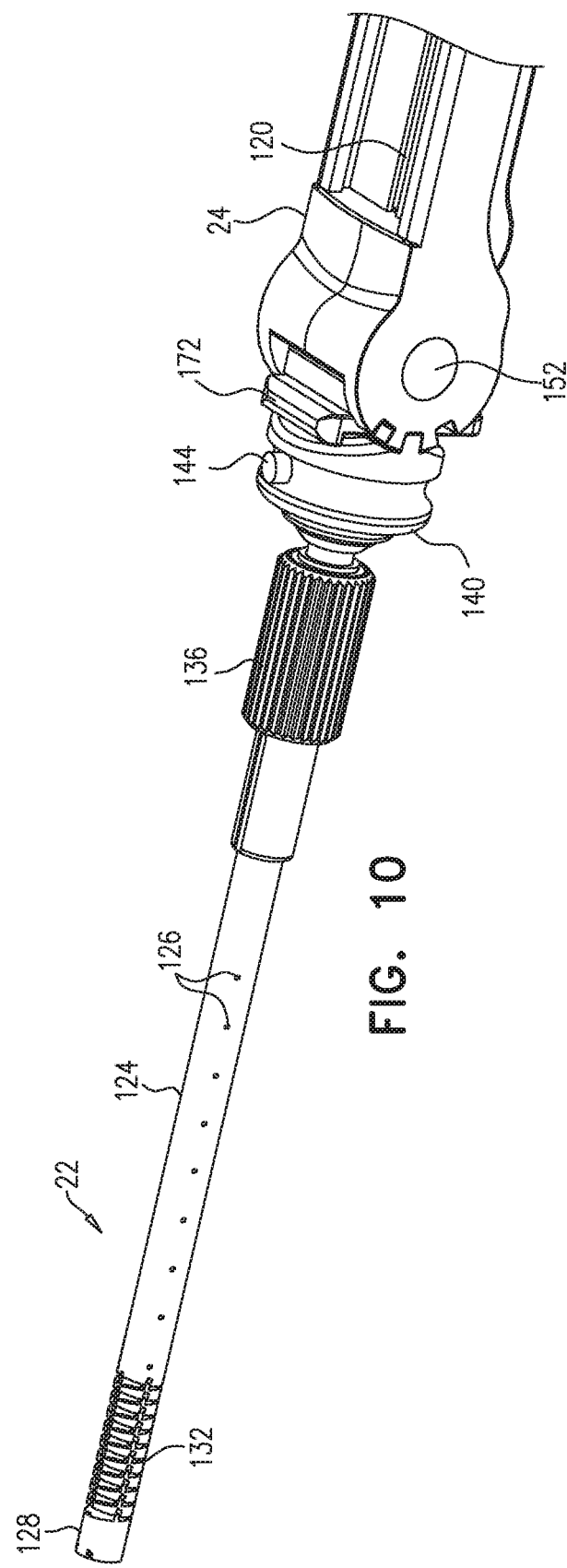
FIG. 10 illustrates a distal section of the manipulator.
Figure 11:
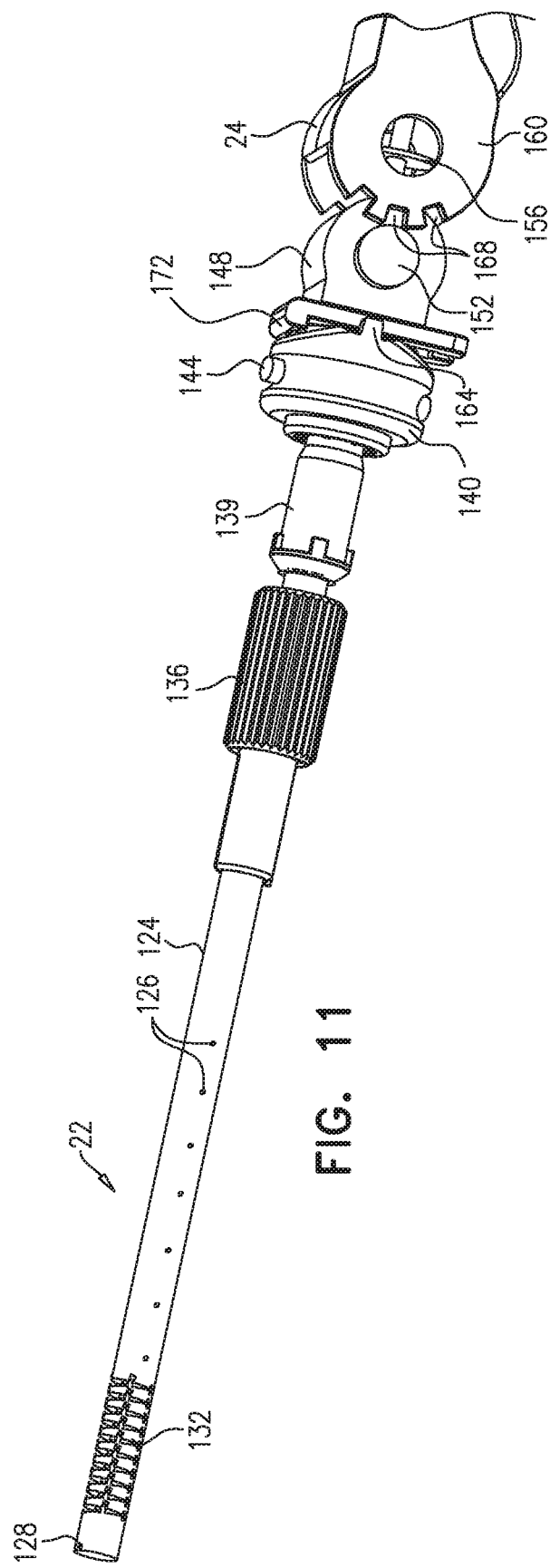
FIG. 11 illustrates the distal section in a partially exploded form, according to an embodiment of the present invention.

FIG. 10 illustrates distal section 22 of manipulator 20, and FIG. 11 illustrates the distal section in a partially exploded form, according to an embodiment of the present invention. Section 22 comprises a rigid tube 124, which is coupled, as described below, to chassis 24 so that a proximal end of the tube aligns with a distal end of passage 120. A distal end 128 of tube 124 is formed of interlocking articulated sections 132, and the sections can be deflected or undeflected by turning of a knurled knob 136 in a clockwise or a counter-clockwise direction. Sections 132 may be coupled to knob 136 by any convenient method known in the art. A method for coupling sections 132 to knob 136 so as to achieve the deflection and undeflection referred to herein is described in U.S. patent application Ser. No. 15/155,850, issued as U.S. Pat. No. 10,820,923 on Nov. 3, 2020. The method uses a metal ribbon, having a curved cross-section, that connects sections 132 to knob 136, so that rotation of the knob translates the ribbon distally or proximally along tube 124. Optionally, tube 124 comprises orifices 126 via which irrigation fluid may be ejected from the tube.

Tube 124 fits fixedly into a tube housing 140, but the tube may be removed from the housing, exposing a cylindrical element 139, as is shown in FIG. 11. The tube may then be rotated, and the element 139 may then be reinserted into the housing, and once in the housing the tube and element 139 may be locked in place with a lock 172. Such removal and reinsertion enables the deflection of sections 132 of distal end 128 to be in any selected direction with respect to the axis of tube 124.

FIGS. 10 and 11 show tube 124 in line with chassis 24. However, the tube may be rotated into one or more fixed positions so that while it is not in line with the chassis a proximal end of the tube still aligns with a distal end of passage 120. To accomplish this rotation, a distal portion 148 of chassis 24 is configured with a protruding axis 152 which is orthogonal to the axis of tube 124. In addition, axis 152 is configured to rotatingly mate with a circular hole 156 in a distal portion 160 of chassis 24, and a tooth 164 in housing 140 can fit into one of a number of receiving indentations 168 in distal portion 160. Once tooth 164 is fit into one of indentations 168, tube 124 may be locked with respect to rotation about axis 152 with a lock 144

The ability of tube 124 to be rotated with respect to chassis 24 facilitates use of manipulator 20 during a sinuplasty procedure, since, as is known, such procedures typically require the use of other tools, such as an endoscope, in confined areas of operation such as the nostrils of a patient.

Figure 12:
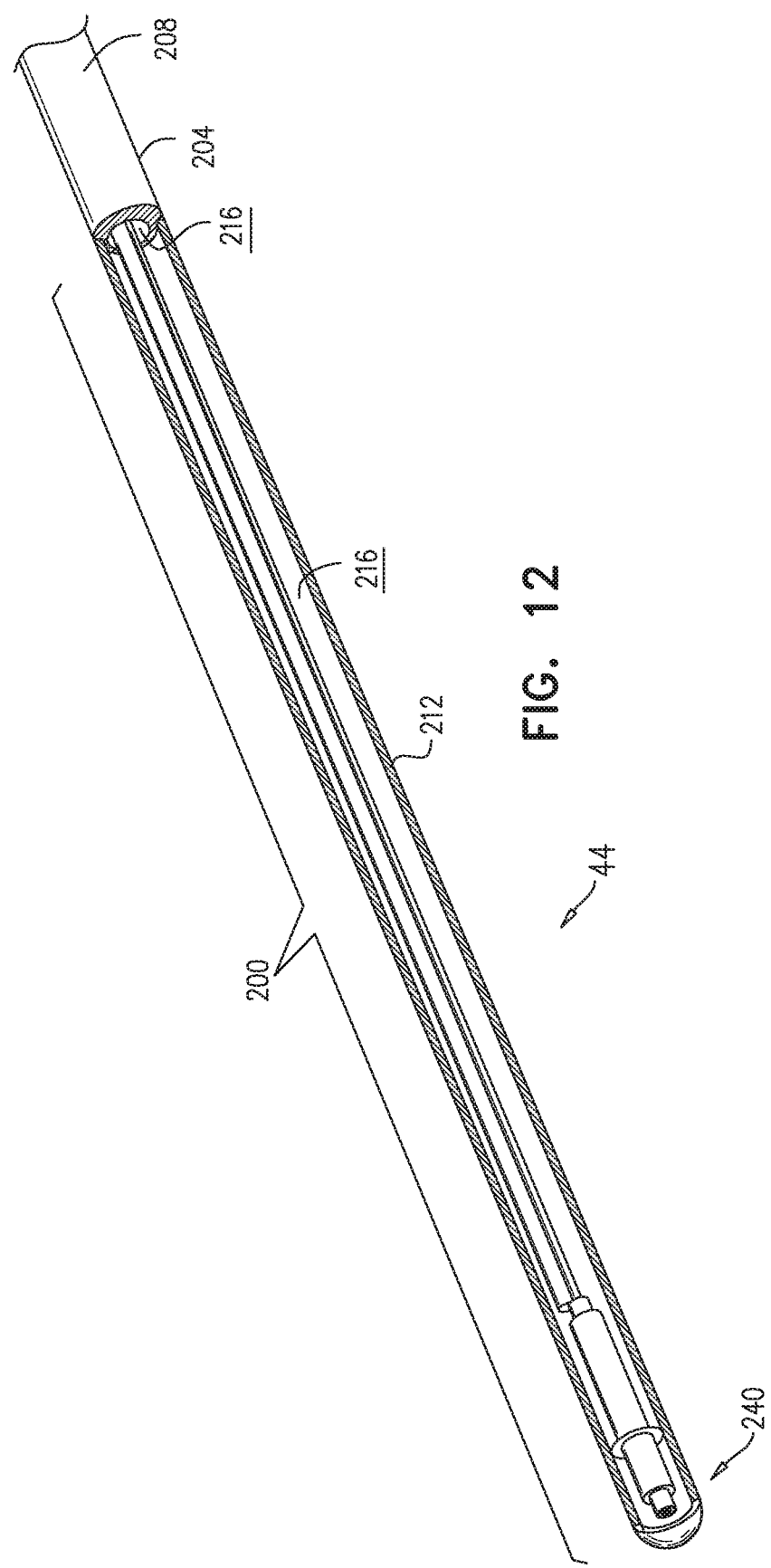
Figure 14:
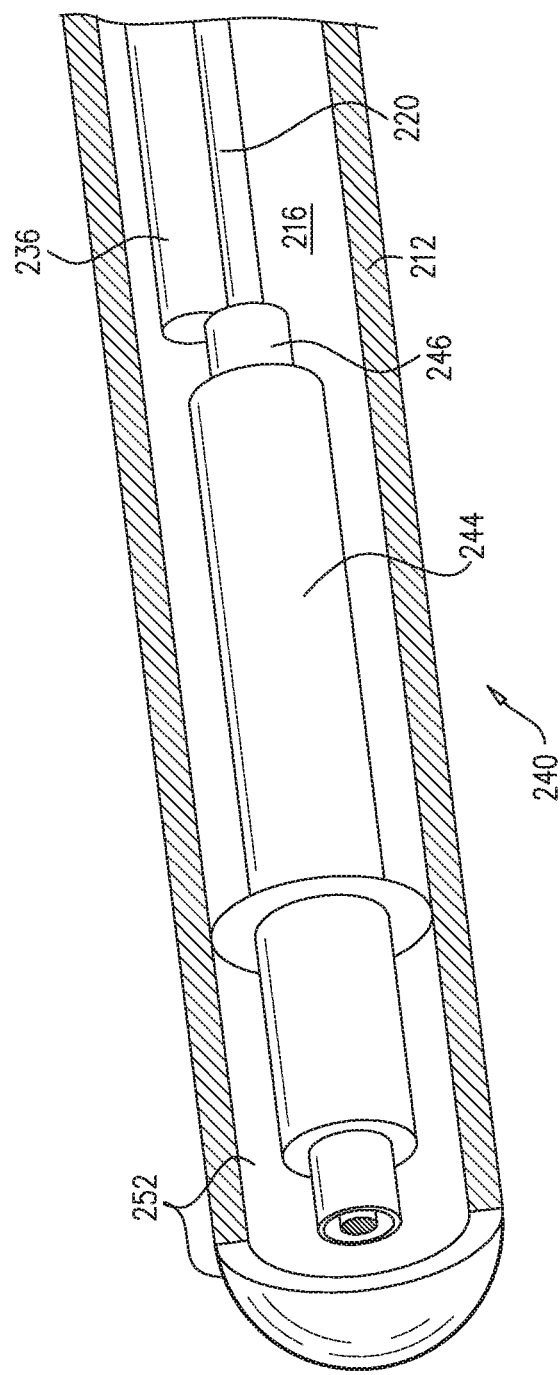

FIGS. 12, 13, and 14 schematically illustrate guidewire 44, according to an embodiment of the present invention. FIG. 12 illustrates a distal portion 200 of the guidewire in a cutaway form, and part of a proximal portion 204 of the guidewire. In one embodiment the overall length of guidewire 44 is approximately 1.3 m, and distal portion 200 is approximately 0.2 m, but other embodiments may have different values for the overall length and for the length of the distal portion.

Proximal portion 204 and distal portion 200 respectively comprise cylindrical plastic tubes 208 and 212. The tubes are cemented together, and form a common lumen 216 within the tubes. A nitinol wire 220 is located in lumen 216 and typically traverses the full length of the guidewire, although in some embodiments it may be shorter.

Tubes 208 and 212 are typically formed from a plastic such as polyimide or polyamide, and each tube is reinforced for example by a braid incorporated into the tube. The braid is typically braided stainless steel. Alternatively, the braid may comprise a braided polymer where the polymer may also be formed from polyimide.

Distal portion 200 is typically configured to be slightly more flexible than proximal portion 204. The difference in flexibility may be achieved by forming the two sections from plastics having different appropriate properties. Alternatively or additionally, tube 208 may be configured to be thicker than tube 212.

FIG. 13 schematically shows cross-sections of tubes 208 and 212, taken orthogonal to an axis 224 of the guidewire. Tube 208 has a braid 228 incorporated into the tube. Tube 212 has a braid 232 incorporated into the tube. Wires 236, in lumen 216, traverse the full length of the guidewire, and the function of the wires is described below.

FIG. 14 schematically shows a distal end 240 of distal portion 200. End 240 comprises a single axis coil 244 which acts as a position sensor. Coil 244 is wound on a polyimide tube 246, the tube being penetrated by nitinol wire 220. Wires 236 (shown in FIG. 14 as a cylinder) connect to the single axis coil, and convey signals generated in the coil back to manipulator 20, and from there to a processor (not shown in the figures). Signals generated by the coil, due to alternating magnetic fields traversing the coil, enable the processor to determine the location and orientation of the coil. Such a system is well known in the art, and is used, for example, in the Carto system produced by Biosense Webster of Technology Drive, Irvine, Calif. 92618 USA.

Distal end 240 is sealed at its tip by a biocompatible cement plug 252 so that lumen 216 is water and air-tight.

In one embodiment, nitinol wire 220 is slightly bent, typically by approximately 15°, so that distal end 240 is also bent with respect to the remaining part of the guidewire.

The inventors have found that the combination of a nitinol wire within one or more plastic tubes, together with braids incorporated in the tubes, prevents kinking of the guidewire.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A manipulator, comprising:
    (a) an elongated chassis containing a U-shaped channel defining a distal direction and a proximal direction; and
    (b) an adjuster configured to slide in the U-shaped channel, the adjuster comprising:
        (i) a first wheel which on rotation translates a guidewire positioned in the adjuster along an axis of the guidewire;
        (ii) a second wheel which on rotation rotates the guidewire positioned in the adjuster about the axis of the guidewire;

(iii) a port, distal to the first wheel and the second wheel, configured to accept a balloon and the guidewire; and (iv) at least one retaining slot configured to allow the first wheel to translate between a non-engaged configuration and an engaged configuration, wherein in the non-engaged configuration the first wheel is configured to not engage the guidewire, wherein in the engaged configuration the first wheel is configured to engage the guidewire, wherein the U-shaped channel contains a passage configured to restrain the balloon and the guidewire from deviating out of the passage.

2. The manipulator according to claim 1, wherein the first wheel comprises a first wheel axle, the at least one retaining slot comprising first and second retaining slots configured to accept the first wheel axle, so that on rotation of the first wheel about the first wheel axle the first wheel slides in the first and second retaining slots to engage the guidewire.

3. The manipulator according to claim 1, wherein the second wheel rotates about a second wheel axis, the adjuster further comprising a plurality of cylinders enclosed by the second wheel and having respective axes parallel to the second wheel axis, so that on rotation of the second wheel about the second wheel axis, the plurality of cylinders move orthogonally to their axes to engage the guidewire.

4. The manipulator according to claim 3, wherein the second wheel contains an open triangular portion, and wherein the plurality of cylinders comprises three cylinders located at respective apices of the triangular portion.

5. The manipulator according to claim 4, wherein on rotation of the second wheel about the second wheel axis, the three cylinders are pushed inwards by sides of the triangular portion so as to engage the guidewire.

6. The manipulator according to claim 1, wherein the balloon is attached in a fluid-tight manner to the port at a proximal end of the balloon.

7. The manipulator according to claim 1, and further comprising a balloon retaining tube, traversing the port, attached to a distal end of the balloon.

8. The manipulator according to claim 1, wherein the balloon translates along the passage when the adjuster slides in the U-shaped channel.

9. The manipulator according to claim 1, and further comprising a rigid tube, removably attached to the elongated chassis, configured to accept the balloon and the guidewire.

10. The manipulator according to claim 9, wherein the rigid tube is attached in a position not in line with the elongated chassis.

11. The manipulator according to claim 1, wherein the first wheel is rotatable about an axis orthogonal to the axis of the guidewire to selectively translate the guidewire in the engaged configuration.

12. A method, comprising:
(a) providing an elongated chassis containing a U-shaped channel defining a distal direction and a proximal direction; and
(b) translating a first wheel of an adjuster using at least one retaining slot of the adjuster from a non-engaged configuration where the first wheel does not engage a guidewire to an engaged configuration where the first wheel engages the guidewire, the adjuster comprising:
(i) the first wheel which on rotation translates the guidewire positioned in the adjuster along an axis of the guidewire,
(ii) a second wheel which on rotation rotates the guidewire positioned in the adjuster about the axis of the guidewire, and
(iii) a port, distal to the first wheel and the second wheel, configured to accept a balloon and the guidewire; and
(c) sliding the adjuster in the U-shaped channel.

13. The method according to claim 12, wherein the first wheel comprises a first wheel axle, the at least one retaining slot comprising first and second retaining slots configured to accept the first wheel axle, so that on rotation of the first wheel about the first wheel axle the first wheel slides in the first and second retaining slots to engage the guidewire.

14. The method according to claim 12, wherein the second wheel rotates about a second wheel axis, the adjuster further comprising a plurality of cylinders enclosed by the second wheel and having respective axes parallel to the second wheel axis, so that on rotation of the second wheel about the second wheel axis, the plurality of cylinders move orthogonally to their axes to engage the guidewire.

15. The method according to claim 14, wherein the second wheel contains an open triangular portion, and wherein the plurality of cylinders comprises three cylinders located at respective apices of the triangular portion.

16. The method according to claim 15, wherein on rotation of the second wheel about the second wheel axis, the three cylinders are pushed inwards by sides of the triangular portion so as to engage the guidewire.

17. The method according to claim 12, and further comprising attaching the balloon in a fluid-tight manner to the port at a proximal end of the balloon.

18. The method according to claim 12, and further comprising attaching a balloon retaining tube, traversing the port, to a distal end of the balloon.

19. The method according to claim 12, wherein the U-shaped channel contains a passage, the method comprising restraining the balloon and the guidewire from deviating out of the passage.

20. The method according to claim 19, and further comprising translating the balloon along the passage when the adjuster slides in the U-shaped channel.

21. The method according to claim 12, and further comprising removably attaching a rigid tube to the elongated chassis, and wherein the rigid tube is configured to accept the balloon and the guidewire.

22. The method according to claim 21, wherein the rigid tube is attached in a position not in line with the elongated chassis.

23. The method according to claim 12, and further comprising rotating the first wheel to translate the guidewire along the axis of the guidewire.

24. A manipulator, comprising:
(a) an elongated chassis defining a distal direction and a proximal direction; and
(b) an adjuster comprising:
(i) a first wheel which on rotation translates a guidewire positioned in the adjuster along an axis of the guidewire, wherein the first wheel comprises a first wheel axle;
(iii) retaining slots configured to accept the axle, so that on rotation of the first wheel about the first wheel axle the first wheel slides in the retaining slots to engage the guidewire;
(iii) a second wheel which on rotation rotates the guidewire positioned in the adjuster about the axis of the guidewire; and (iv) a port, distal to the first wheel and the second wheel, configured to accept a balloon and the guidewire.

25. The manipulator according to claim 24, wherein the elongated chassis contains a U-shaped channel, wherein the adjuster is configured to slide in the U-shaped channel.

26. The manipulator according to claim 24, wherein the balloon is attached in a fluid-tight manner to the port at a proximal end of the balloon.

27. A manipulator, comprising:
(a) an elongated chassis defining a distal direction and a proximal direction; and
(b) an adjuster comprising:
(i) a first wheel which on rotation translates a guidewire positioned in the adjuster along an axis of the guidewire;
(ii) a second wheel which on rotation rotates the guidewire positioned in the adjuster about the axis of the guidewire, wherein the second wheel rotates about a second wheel axis;
(iii) a plurality of cylinders enclosed by the second wheel and having respective axes parallel to the second wheel axis, so that on rotation of the second wheel about the second wheel axis, the plurality of cylinders move orthogonally to their axes to engage the guidewire; and
(iv) a port, distal to the first wheel and the second wheel, configured to accept a balloon and the guidewire.

28. The manipulator according to claim 27, wherein the elongated chassis contains a U-shaped channel, wherein the adjuster is configured to slide in the U-shaped channel.

29. The manipulator according to claim 27, wherein the second wheel contains an open triangular portion, and wherein the plurality of cylinders comprises three cylinders located at respective apices of the triangular portion.

30. The manipulator according to claim 27, wherein the balloon is attached in a fluid-tight manner to the port at a proximal end of the balloon.

\* \* \* \* \*